US012691033B2

(12) United States Patent
Evans, II et al.

(10) Patent No.: US 12,691,033 B2
(45) Date of Patent: Jul. 28, 2026

(54) LYOPHILIZED CAKE IN STRAIGHT-WALLED VIAL

(71) Applicant: Elanco US Inc., Greenfield, IN (US)

(72) Inventors: Donald D. Evans, II, Greenfield, IN (US); Mayur Patel, Greenfield, IN (US); Lee J. Stimpson, Greenfield, IN (US)

(73) Assignee: Elanco US Inc., Indianapolis, IN (US)

( * ) Notice: Subject to any disclaimer, the term of this patent is extended or adjusted under 35 U.S.C. 154(b) by 285 days.

(21) Appl. No.: 17/778,147

(22) PCT Filed: Nov. 5, 2020

(86) PCT No.: PCT/US2020/059074
§ 371 (c)(1),
(2) Date: May 19, 2022

(87) PCT Pub. No.: WO2021/101720
PCT Pub. Date: May 27, 2021

(65) Prior Publication Data
US 2022/0409484 A1 Dec. 29, 2022

Related U.S. Application Data

(60) Provisional application No. 62/937,061, filed on Nov. 18, 2019.

(51) Int. Cl.
| *A61J 1/14* | (2023.01) |
| *A61J 1/06* | (2006.01) |
| *A61K 9/19* | (2006.01) |
| *A61K 39/02* | (2006.01) |

(52) U.S. Cl.
CPC ............. *A61J 1/1468* (2015.05); *A61J 1/065* (2013.01); *A61J 1/1406* (2013.01); *A61K 9/19* (2013.01); *A61K 39/099* (2013.01)

(58) Field of Classification Search
CPC .... A61J 1/065; A61J 1/00; A61K 9/19; A61K 39/099; A61L 2202/23
See application file for complete search history.

(56) References Cited

U.S. PATENT DOCUMENTS

| 3,640,437 | A | | 2/1972 | Galy | |
| 5,733,555 | A | * | 3/1998 | Chu | A61P 31/14 |
| | | | | | 424/211.1 |
| 8,574,213 | B2 | | 11/2013 | Thilly et al. | |
| 2008/0031949 | A1 | | 2/2008 | Hamed et al. | |
| 2010/0260796 | A1 | | 10/2010 | Belin-Poput et al. | |

(Continued)

FOREIGN PATENT DOCUMENTS

| JP | H053904 A | 1/1993 |
| JP | 1998-500113 A | 1/1998 |

(Continued)

OTHER PUBLICATIONS

English Translation of Russian Search Report issued for Application No. 2022116315, mailed Apr. 24, 2024.

(Continued)

*Primary Examiner* — Jessica Arble
(74) *Attorney, Agent, or Firm* — Barnes & Thornburg LLP

(57) ABSTRACT
A system including a vial and methods of its use to provide a lyophilized cake removable from the vial without cracking or breaking.

19 Claims, 4 Drawing Sheets

(56) References Cited

U.S. PATENT DOCUMENTS

| | | | | |
|---|---|---|---|---|
| 2012/0283689 | A1* | 11/2012 | Thilly | B65D 51/241 |
| | | | | 604/411 |
| 2013/0273100 | A1* | 10/2013 | O'Connell | A61K 39/12 |
| | | | | 424/201.1 |
| 2014/0287043 | A1* | 9/2014 | Kaplan | A61K 9/7007 |
| | | | | 424/234.1 |
| 2015/0283030 | A1* | 10/2015 | Skufca | A61J 1/1481 |
| | | | | 53/489 |
| 2018/0256699 | A1 | 9/2018 | Wang et al. | |
| 2019/0194628 | A1* | 6/2019 | Rao | A61K 39/13 |

FOREIGN PATENT DOCUMENTS

| | | | | |
|---|---|---|---|---|
| JP | 10234822 | A | * | 9/1998 |
| JP | H10234822 | A | | 9/1998 |
| JP | 2008-518189 | A | | 5/2008 |
| JP | 2009-513381 | A | | 4/2009 |
| JP | 2012125436 | A | | 7/2012 |
| JP | 2014-500302 | A | | 1/2014 |
| JP | 2015-189497 | A | | 11/2015 |
| JP | 2016-500312 | A | | 1/2016 |
| JP | 2018-533547 | A | | 11/2018 |
| JP | 2019-507784 | A | | 11/2018 |
| JP | 2019-177040 | A | | 10/2019 |
| KR | 20070084561 | A | | 8/2007 |
| RU | 2039570 | C1 | | 7/1995 |
| RU | 2369635 | C2 | | 1/2009 |
| RU | 2356577 | C9 | | 8/2009 |
| RU | 2407787 | C1 | | 12/2010 |
| RU | 2529959 | C1 | | 10/2014 |
| RU | 2605822 | C2 | | 12/2016 |
| RU | 2017128106 | A3 | | 2/2019 |
| WO | 95/30437 | | | 11/1995 |
| WO | 2004061093 | A1 | | 7/2004 |
| WO | 2004037189 | A2 | | 10/2004 |
| WO | 2005/005128 | A1 | | 1/2005 |
| WO | 2006045625 | A1 | | 5/2006 |
| WO | 2012/085642 | A1 | | 6/2012 |
| WO | 2012104821 | A1 | | 8/2012 |
| WO | 2014/026721 | A1 | | 2/2014 |
| WO | 2017/047089 | A1 | | 3/2017 |
| WO | 2017/187277 | A2 | | 11/2017 |

OTHER PUBLICATIONS

Regina Hofmann-Lehmann and Katrin Hartmann, "Feline leukaemia virus infection: A practical approach to diagnosis" J Feline Med Surg. Sep. 2020; 22(9): 831-846.

International Search Report and Written Opinion prepared for PCT/US2020/059074, mailed Nov. 12, 2020.

Petrukhina, A.T. and Blinova, E.I. "Bacterial and viral preparations" Academy of Natural Sciences, 2010.

Zhukova, N.V. and Krivosheeva, I.M. "Modern vaccines: characterization and classification" Crimean Therapeutic Journal (KTZ), N2, 2013, p. 831-846.

* cited by examiner

LYOPHILIZED CAKE IN STRAIGHT-WALLED VIAL

CROSS-REFERENCE TO RELATED APPLICATIONS

This application is a national stage entry under 35 USC § 371 (b) of PCT International Application No. PCT/US2020/059074, filed Nov. 5, 2020, which claims the benefit of, and priority from, U.S. Provisional Application No. 62/937,061, filed Nov. 18, 2019, both of which are incorporated herein by reference in their entirety.

FIELD OF THE DISCLOSURE

The disclosure relates generally to a system comprising a straight-walled vial and its use thereof to provide a removable lyophilized cake.

BACKGROUND OF THE DISCLOSURE

Development of stable, safe, and efficacious biopharmaceuticals relies in large part on the use of appropriate container systems. These systems are necessary to store and safeguard the otherwise fragile biopharmaceutical compositions from factors which promote degradation and destabilization. Lyophilization is a commonly-employed freeze-drying process which yields a stable dried or powdered product, often a lyophilized cake, inside the lyophilization processing vial. Existing vials for lyophilization, however, contain a neck, so the resulting cake can never be removed in an intact form.

A removable lyophilized cake would be a therapeutically useful oral or injectable option for presentation of a biopharmaceutical, such as a vaccine.

SUMMARY

In one aspect of the disclosure, a system to provide a lyophilized cake removable from a vial without cracking or breaking is provided. In embodiments according to the first aspect, a straight-walled vial system comprises: a straight-walled vial; and a solid lyophilized vaccine composition within the straight-walled vial, the composition comprising an antigen and a stabilizer.

In some variations of the present embodiment, the antigen source is animal, human, fish, bird, microorganism, parasite, protozoal, spirochete, bacterial, viral, vector, recombinant, or combination thereof; and the antigen is a nucleic acid, protein, peptide, or combination thereof.

In a second aspect of the disclosure, a method to provide a lyophilized cake removable from a vial without cracking or breaking is provided. In embodiments according to the second aspect, a method for preparing a solid lyophilized vaccine composition comprises: combining an antigen and a stabilizer to obtain a blend; filling a straight-walled vial with the blend; lyophilizing the blend in the straight-walled vial to form a solid lyophilized vaccine composition; and removing the solid lyophilized vaccine composition from the straight-walled vial.

In some variations of the present embodiment, the method comprises adding mannitol to the blend of antigen and stabilizer and further comprises annealing the blend at −25° C. prior to removing the solid lyophilized vaccine composition

Figures 1, 2:
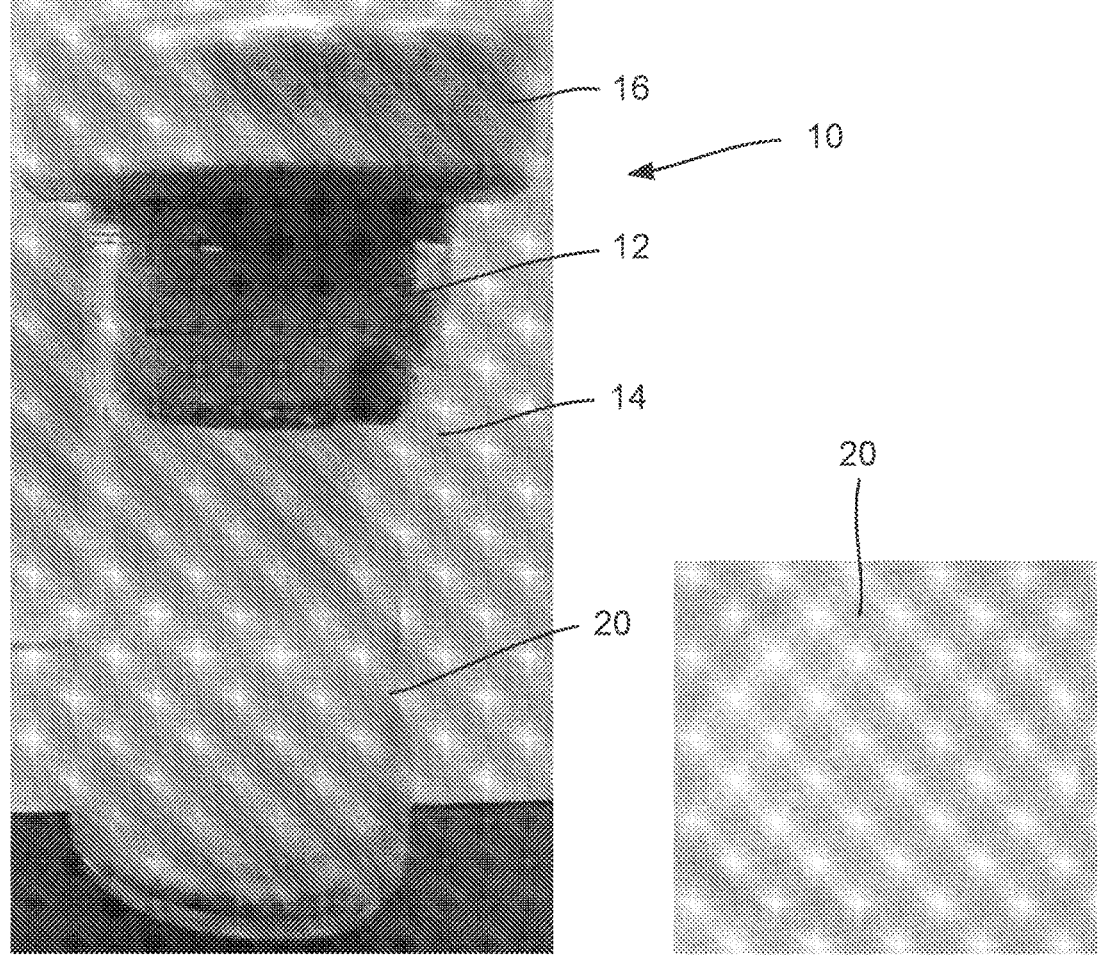
FIG. 1 is a perspective view of an embodiment of a straight-walled vial system including a straight-walled vial.
FIG. 2 is a perspective view of an embodiment of a cake removed from the straight-walled vial of FIG. 1 in intact form.

In the drawings, corresponding reference characters indicate corresponding parts, functions, and features throughout the several views. Although the drawings represent embodiments of various features and components according to the present invention, the drawings are not necessarily to scale and certain features may be exaggerated in order to better illustrate and explain the present invention. However, the invention is not limited to the precise arrangements and instrumentalities of the embodiments shown in the drawings.

DETAILED DESCRIPTION OF DISCLOSED EMBODIMENTS

For the purposes of promoting an understanding of the principles of the disclosed embodiments, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention as set forth in the claims.

FIG. 1 is a perspective view of an embodiment of a straight-walled vial system 10 in an assembled state, including a straight-walled vial 14, a stopper 12, a seal 16, and a cake 20. The seal 16 may comprise aluminum and is crimped over the stopper 12 in any known manner. The seal 16 may alternatively comprise plastic. In a variation, the stopper 12 and seal 16 may be configured as a single unit, and this unit may be configured such that a portion of the unit may be removed, such as with a tab. In such an example, the tab may be removed to insert a syringe or needle.

FIG. 2 is a top view of the cake 20 removed from the straight-walled vial system 10. In some embodiments, the cake 20 is a lyophilized drug or biopharmaceutical product. The dimensions of the cake 20 may be customized by altering the height and cross-section of the straight-walled vial 14 to allow for larger or smaller resulting cakes 20, in part depending on the animal or human of eventual administration. In some embodiments, the cake 20 is designed to be administered in solid form. The cake 20 may alternatively be dissolved before administration.

Figures 3, 4, 5:
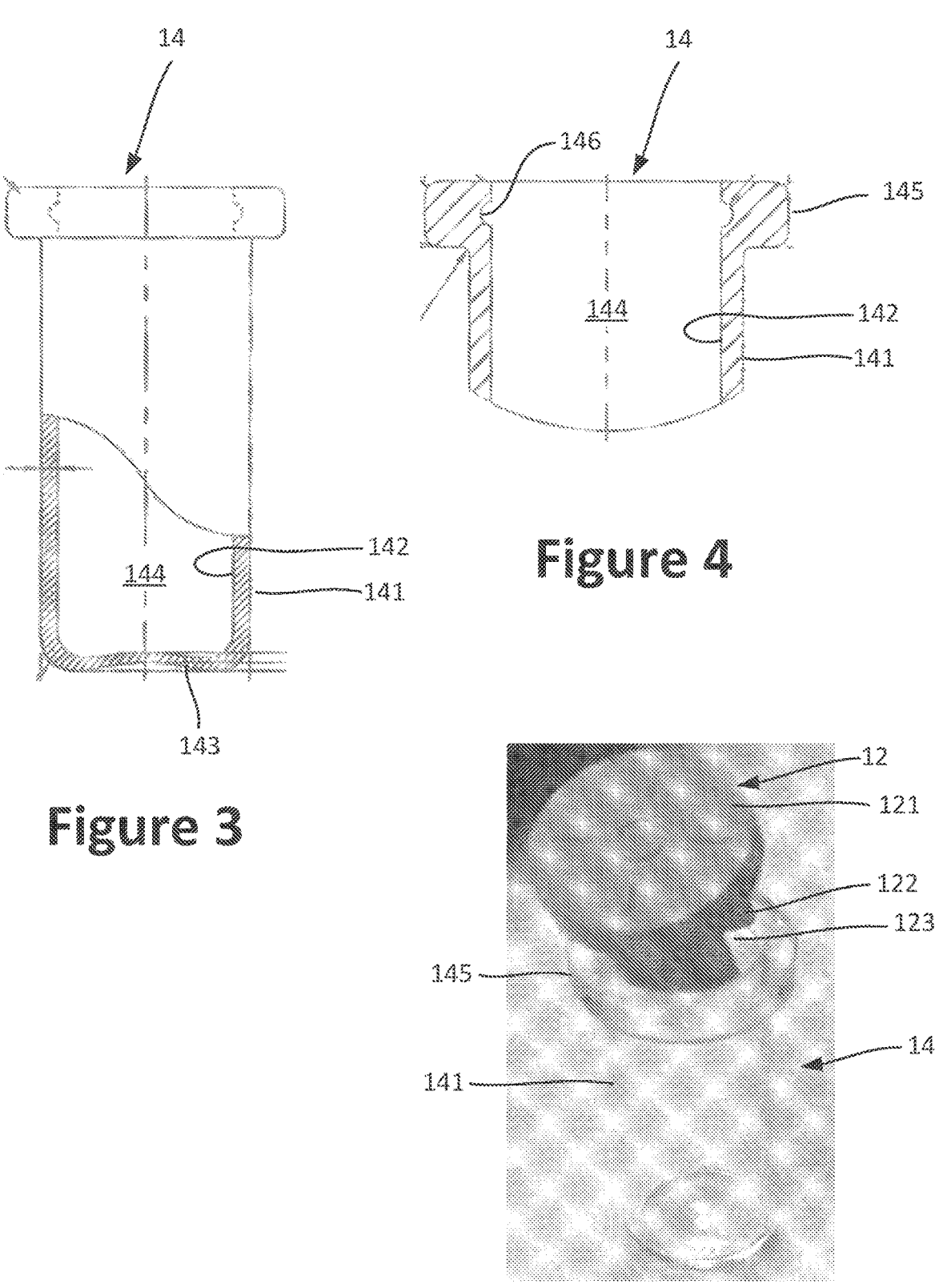
FIG. 3 is a side view of an embodiment of the straight-walled vial shown in FIG. 1.
FIG. 4 is a sectional view of the embodiment of the straight-walled vial of FIG. 3.
FIG. 5 is a perspective view of components of the embodiment of the straight-walled vial system of FIG. 1.

FIG. 3 is a side view of an embodiment of the straight-walled vial 14 shown in FIG. 1. The straight-walled vial 14 includes a side wall 141, an inner surface 142, a bottom wall 143, and a collar 145 surrounding the top end (opposite the bottom wall 143) of the straight-walled vial 14. The side wall 141 extends perpendicularly from the bottom wall 143 to the collar 145 and may include a circumferential inner slot 146 intermediate the width of the collar 145 extending radially outwardly from the inner surface 142. The slot may allow for easier removal of a stopper 12, for example, when a straight-walled vial 14 has been sealed using a vacuum or the like. The side wall 141 and the bottom wall 143 define an inner volume 144 of the straight-walled vial 14. As used herein, "straight-walled" means that the side wall of the vial is not necked-in and the term is not limited to vials with side walls exactly perpendicular to the bottom wall. For example, the cross-section of the vial across its length may gradually increase from the bottom wall to the collar, and such a frustoconical vial would also allow removal of an intact cake. The cake may shrink in the process of making it, therefore the cross-section may also gradually decrease, so long as the cross-section is never smaller than the cross-section of the cake.

In some embodiments, the straight-walled vial 14 comprises or is made from a polymeric material. In other embodiments, the straight-walled vial 14 comprises or is made from glass. In other embodiments, the straight-walled vial 14 comprises or is made from other materials that can withstand routine lyophilization temperatures and pressures.

In some embodiments, the straight-walled vial 14 is a 15×35 mm vial.

In some embodiments, the straight-walled vial 14 has an outer diameter of 15±0.25 mm.

In some embodiments, the side wall 141 is 35±0.05 mm in height. In some embodiments, the side wall 141 is 1.2±0.05 mm thick.

In some embodiments, the side wall 141 is thinner than standard lyophilization vials to allow for optimal heat transfer during lyophilization.

In some embodiments, the bottom wall 143 has a minimum thickness of 0.70 mm.

In some embodiments, the bottom radius of the straight-walled vial 14 is 1.47 mm to 2.49 mm.

In some embodiments, the bottom wall 143 has a bottom push-up of 0.2 mm-0.8 mm and a bottom slant of 0.3 mm max.

In some embodiments, the inner volume 144 is 0.3 mL, 0.5 mL, 1 mL, 1.5 mL, 2 mL, 3 mL, 5 mL, 10 mL, or 20 mL.

In some embodiments, the straight-walled vial 14 is cylindrically shaped with an outer diameter of about 15±0.25 mm and a length of about 35±0.05 mm. The side wall 141 may be 1.2±0.05 mm thick. The bottom wall 143 may have a minimum thickness of 0.70 mm.

FIG. 4 is a side view of an embodiment of a straight-walled vial 14 which includes a side wall 141, inner surface 142, inner volume 144, collar 145, and slot 146. In some embodiments, the collar 145 allows the straight-walled vial to be configured with a stopper 12 and a seal 16, such that the seal 16 can be crimp sealed over the collar 145. The inner slot 146 can fit with a corresponding outer ridge on a stopper 12. In some embodiments, the inner radius from one inner surface 142 to another is 12.6±0.2 mm. In some embodiments, the collar 145 has a height of 3.4 mm-3.78 mm. In some embodiments, the slot 146 is configured to have a blowback.

FIG. 5 is a perspective view of the straight-walled vial 14 with a partially-inserted stopper 12. The stopper 12 includes a head 121, a neck 122 extending from and having a smaller cross-section than the head, and a slot 123 splitting at least a portion of the neck. The slot 123 can serve as a vent for water vapor transfer during lyophilization.

In some embodiments, the stopper 12 is a standard 20 mm serum stopper or a lyophilizing stopper.

In some embodiments, the stopper 12 comprises or is made from rubber.

Figure 6:
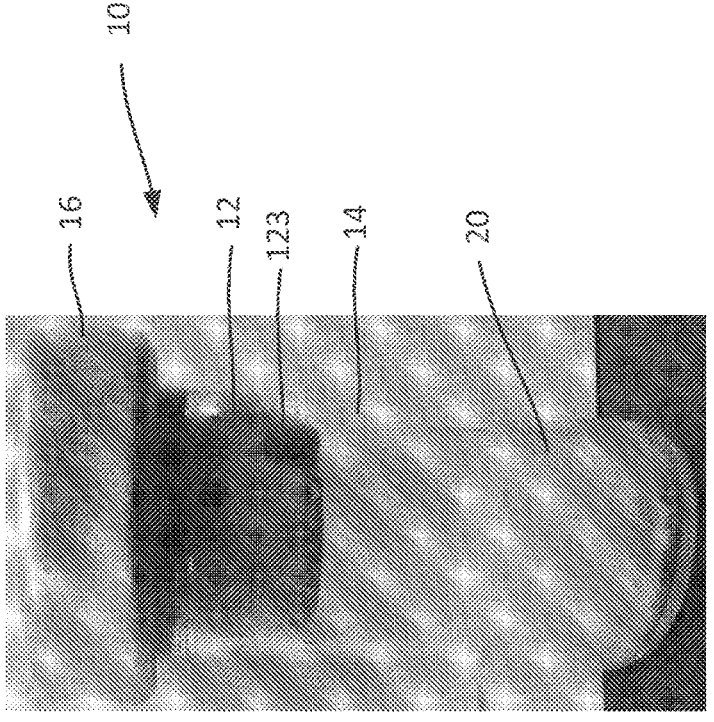
FIG. 6 is a perspective view of the embodiment of the straight-walled vial system of FIG. 1 showing the cake at the bottom of the straight-walled vial.

FIG. 6 is a perspective view of the embodiment of the straight-walled vial system 10 depicted in FIG. 1, showing the cake 20 is deposited on the bottom wall 143 of the straight-walled vial 14. In some embodiments, the cake 20 may separate from the inner surface 142 and rise slightly from the bottom wall 143.

Figure 7:
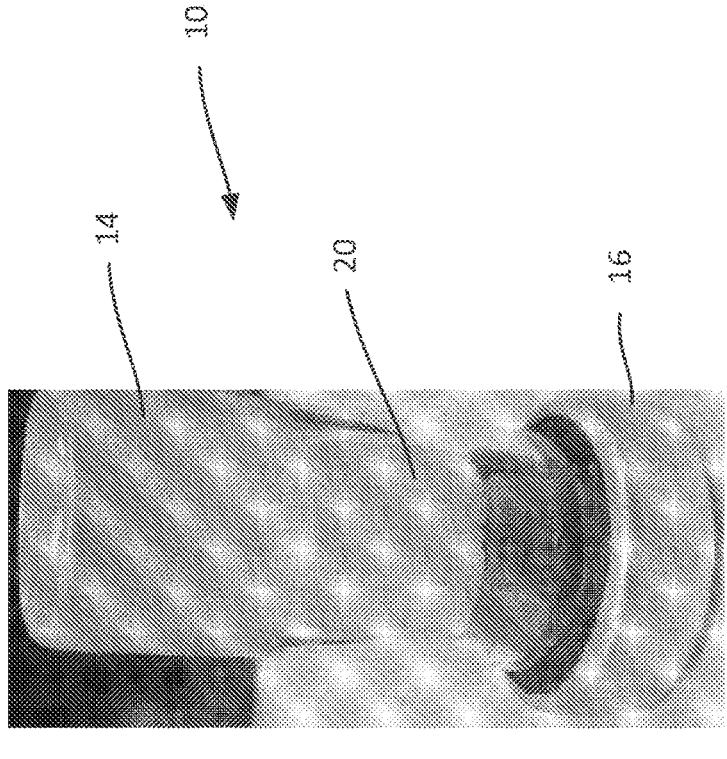
FIG. 7 is a perspective view of the embodiment of the straight-walled vial system of FIG. 1 showing the cake at the top of the straight-walled vial.

FIG. 7 is a perspective view of the straight-walled vial system 10 turned upside-down showing that the cake 20 separates from the bottom wall 143 and inner surface 142 and moves freely within the inner volume 144, so that in this view, the cake 20 is deposited on the stopper 12. Upon removal of the seal 16 and the stopper 12 the cake 20 can be removed substantially intact from the straight-walled vial 14.

Figure 8:
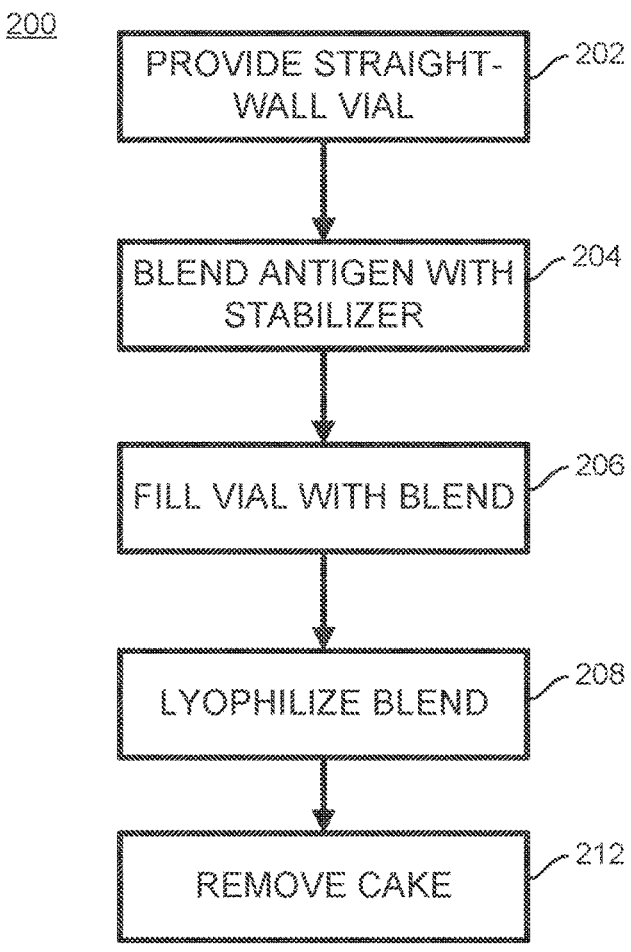
FIG. 8 is a representative flow diagram depicting an embodiment of a method of use for a straight-walled vial system.

FIG. 8 is a representative flow diagram depicting an embodiment of a method of use for a straight-walled vial system 10, the method comprising: providing a straight-walled vial, at 202; blending antigen with a stabilizer, at 204; filling the vial with the blend, at 206; lyophilizing the blend, at 208; and removing the cake, in substantially intact form, at 212.

In some embodiments of the disclosed method of use, the antigen is any medicament, compound, or drug used to prevent or treat a disease or condition. In a variation, the composition is an antigenic composition. In a variation, the antigenic composition can cause an immune response or be involved in a biological activity. In some embodiments, the antigen can be of animal origin. For example, the antigen can be from a mammal, such as a human. In some examples, the antigen can be from a non-mammal, such as a fish or a bird. In other examples the antigen can be from a microorganism or from a parasitic organism. For example, the antigen can of bacterial, viral, or fungal origin. In some examples, a bacterial antigen can be from a spirochete. In other examples, the antigen can be derived from a bacterial vector or a viral vector, or from a recombinant source thereof. In some embodiments, the antigen can be a nucleic acid, protein, peptide, or combination thereof. In some embodiments, the antigen can be a live, modified live, or inactivated microorganism. For example, the antigen can be derived from or be used to prevent or treat one or more pathogenic infections, which include but are not limited to *Bordetella bronchiseptica* (Bb), Rabies Virus, Canine Influenza Virus (CIV), Canine Adenovirus-2 (CAV2), Canine Adenovirus-1 (CAV1), Canine Distemper Virus (CDV), Canine Parainfluenza (CPiV), Canine Parvo Virus (CPV), Feline Calicivirus (FCV), Feline Herpes Virus (FHV), Feline Panleukopenia Virus (FPL), Feline leukemia Virus (FeLV), *Borrelia, Ehrlichia*, and Giardia. In some embodiments, the antigen can be formulated with a pharmaceutical carrier or the like.

In some embodiments of the disclosed method of use, the solid lyophilized composition is a vaccine for use in an animal subject. For example, the animal subject may be a mammal, such as a human, cow, pig, cat, dog, horse, rabbit, or wild animal. In other examples, the subject may be a non-mammal, such as a fish or bird.

In some embodiments of the disclosed method of use, the antigen can be blended with an adjuvant, an immunoadjuvant, or an immunomodulator, or a combination thereof. In a variation, this includes any compound that enhances the immunogenicity or physiological efficacy of the composition when administered as a mixture.

In some embodiments of the disclosed method of use, the antigen can be blended with a bulking agent. In a variation, the bulking agent can be used to strengthen the resulting cake, and/or to make the resulting cake more intact. For example, the bulking agent can be mannitol, starch, gelatin, or a combination thereof.

In some embodiments of the disclosed method of use, the antigen can be blended with a mucoadhesive agent. In a variation, the mucoadhesive agent can increase the efficacy of the interaction of the compound with the mucosal membrane. In some embodiments, the antigen can be blended with an agent that enhances mucosal permeability.

In some embodiments of the disclosed method of use, when blending antigen with stabilizer, antigen comprises up to 50% of the total blend. In some embodiments, antigen comprises up to 75% of the total blend. A determination of the percentage antigen to be used in the total blend can be made based on the dose, stability data, and loss on drying.

In some embodiments of the disclosed method of use, when blending antigen with stabilizer, the stabilizer can be, but is not limited to the SGGK3 stabilizer, as disclosed herein. In some embodiments, SGGK3 stabilizer is comprised of two solutions, SGGK3 Sol. 1 and SGGK3 Sol. 2. In some embodiments, SGGK3 Sol.1 comprises 60% of the SGGK3 stabilizer and SGGK3 Sol. 2. comprises 40% of the overall stabilizer. The composition of SGGK3 Sol. 1 and SGGK3 Sol. 2. is provided below, in Table 1.

In some embodiments of the disclosed method of use, when blending antigen with stabilizer, stabilizer comprises 50% of the total blend. In some embodiments, stabilizer comprises 25% of the total blend. In some embodiments, stabilizer comprises 20%-30% of the total blend.

TABLE 1

| Component | % in SGGK3 Sol. 1 | Final % in Blend |
|---|---|---|
| SGGK3 Sol. 1 | | |
| Bacto Peptone | 6% | 0.9% |
| Sucrose | 25% | 3.755 |
| Potassium Phosphate Dibasic | 0.4167% | 0.063% |
| Potassium Phosphate Monobasic | 0.1717% | 0.026% |
| Potassium Hydroxide | 0.0913% | 0.014% |
| Mannitol (Optional) | 12% | 1.8% |
| Xanthan Gum (Optional) | 0.084% | 0.013% |
| SGGK3 Sol. 2. | | |
| Gelatin | 10% | 1% |

In some embodiments of the disclosed method of use, when blending antigen with stabilizer, blending diluent comprises up to 25% of the total blend. In some embodiments, blending diluent is added to QS (quantity sufficient) the blend to its final volume and can vary depending on the addition of antigen. The composition of an embodiment of blending diluent is provided in Table 2, below.

TABLE 2

| | Blending Diluent | |
|---|---|---|
| Component | % in SGGK3 Sol. 1 | Final % in Blend |
| MEM Powder | 0.96% | Up to 0.72% |
| Sodium Bicarbonate | 0.105% | Up to 0.079% |
| HEPES Acid QSed with Purified Water | 0.4766% | Up to 0.357% |

Generally, lyophilizing (aka freeze drying) is a process in which a formulation containing a substance dissolved in a suitable solvent is frozen and then vacuumed, which allows the ice to sublimate rather than pass through the liquid phase of thawing. Standard lyophilization techniques for the production of freeze-dried vaccines are well known.

In a variation of a present embodiment, when the antigen and stabilizer composition includes a crystalline component, the lyophilize blend step, at 208, may include an additional annealing step. In variations, this annealing step can be at −25° C. and can allow for a re-formation of the crystals into a stronger structure in the formulation. For example, this step can be used when the formulation is one that comprises mannitol.

In some embodiments of the disclosed method of use, the cake has shrunk in comparison to the inner surfaces of the straight-walled vial 14 and can move within the inner volume 144.

In some embodiments of the disclosed method of use, when removing cake, the straight-walled vial 14 can be turned upside down, as depicted in FIG. 7, and the cake 20 can fall through gravity to rest on the stopper 12, or if the straight-walled vial 14 has had the stopper 12 removed, the cake 20 can be removed from the straight-walled vial 14 entirely. In some embodiments, the cake removal results in minimal loss of viability in the cake and/or minimal residue left on the inner surface 142 of the straight-walled vial 14. Minimal loss may be a reduction of 5% or less. In some embodiments, the cake can be removed from the straight-walled vial 14 without physically cracking or breaking of the cake.

EXAMPLES

Example 1: Glass Straight-Walled Vials with Stabilizer Formulation

According to embodiments of the methods of the present disclosure, a glass straight-walled vial system can be used to generate a removable cake of a lyophilized formulation.

In one embodiment, test groups blended 50% *Bordetella bronchiseptica* antigen with 50% stabilizer (n=5 each): SGGK3 Stabilizer, SGGK3 with mannitol and Xanthan Gum (bulking agent and mucoadhesive), Cuxhaven Stabilizer B (current poultry stabilizer), or Cuxhaven with Mannitol and Xanthan Gum (bulking agent and mucoadhesive). The blends were sampled for viable counts (see Table 3, below) and were added to straight-walled glass vials at 1.2 mL or 0.5 mL. The straight-walled vials were lyophilized via cycles of 60-360 minutes at 60 mTorr at −50° C. to 28° C., with an additional −25° C. annealing step to allow for proper crystal formation (due to the mannitol addition).

Each straight-walled vial was evaluated for viable plate counts prior to lyophilization and post-lyophilization, both in the vial and post-removal.

In-vial assessment Post Lyophilization, 1.2 mL vial were reconstituted with 1.2 mL of PBS each and pooled to assess viable counts, as depicted in Table 3, below. Post Lyophilization cakes were removed from the vials, placed in a 50 mL C tube, pooled (cakes from 5 vials per condition) and reconstituted with 6 mL of PBS to assess viable counts, see Table 3.

The formulations containing SGGK3 stabilizer resulted in an acceptable lyophilized appearance in the straight-walled vials, the Cuxhaven B Formulations resulted in a poor appearance in the straight-walled vials and some of the formulations containing Cuxhaven B appeared to not have completely dried.

The cakes resulting from the formulations containing SGGK3 stabilizer were easily removed from the straight-walled vials with a slight tap to the vial, and left little residue in the vials. The formulations containing Cuxhaven B were not removable from the straight-walled vials. All formulations in the straight-walled vials showed a minimal loss on drying (as indicated Table 3).

As depicted in Table 3, the cakes resulting from the formulations containing SGGK3 stabilizer resulted in no loss of viable counts when removed from the vial as a cake.

TABLE 3

| | | Viable Counts | | | | |
|---|---|---|---|---|---|---|
| Serial | Stabilizer | Pre-Lyophilization | Post-Lyophilization in Vial | Post-Lyophilization Cake | Residual in Vial | % Residual |
| 4028-053A | SGGK3 | 4.57E+09 | 4.67E+09 | 4.87E+09 | 6.80E+06 | 0.140% |
| 4028-053B | SGGK3 with Mannitol and Xanthan Gum | 4.00E+09 | 4.17E+09 | 4.57E+09 | 1.30E+07 | 0.284% |
| 4028-053C | Cuxhaven B | 4.07E+09 | 3.89E+09 | | | |
| 4028-053D | Cuxhaven B with Mannitol and Xanthan Gum | 4.17E+09 | 3.60E+09 | | | |

The cakes resulting from the formulations containing SGGK3 stabilizer were functional, see Table 4, below.

TABLE 4

| | Dispersion Time (sec) | |
|---|---|---|
| Cake | 4028--053A | 4028-053B |
| 1 | 0.45 | 0.62 |
| 2 | 0.23 | 0.74 |
| 3 | 0.53 | 0.43 |
| Average | 0.40 | 0.60 |

Example 2: Glass and Plastic Vials with Stabilizer Formulation

According to embodiments of the methods of the present disclosure, a plastic vial system can be used to generate a removable cake of a lyophilized formulation comparable to the removeable cake generated using glass straight-walled vials.

In one embodiment, test groups blended 50% live *Bordetella bronchiseptica* antigen with Stabilizer (25% SGGK3 with 25% Blending Diluent). The blends were sampled for viable counts (see Table 5, below) and were added to either glass straight-walled vials at 1.2 mL or 0.3 mL per vial (n=20 each) or plastic 3 mL straight-walled vials at 1.2 mL or 0.5 mL (n=20 each). The straight-walled vials were lyophilized as detailed above in Example 1.

Once drying was complete, for in-vial assessment Post Lyophilization, 1.2 mL vials were reconstituted with 1.2 mL of PBS each and pooled (5 vials) to assess viable counts, as depicted in Table 5, below.

The cakes resulting from the formulations containing SGGK3 stabilizer were easily removed from the straight-walled glass vials.

TABLE 5

| | | | Viable Counts | |
|---|---|---|---|---|
| Serial | Stabilizer | | Pre-Lyo | Post Lyo in Vial |
| 4028-075AP | SGGK3 | Plastic | $1.86 \times 10^9$ | $5.97 \times 10^8$ |
| 4028-075AG | SGGK3 | Glass | | $8.3 \times 10^8$ |
| 4028-075BP | SGGK3 w/Mannitol | Plastic | $1.9 \times 10^9$ | $7.7 \times 10^8$ |
| 4028-075BG | SGGK3 w/Mannitol | Glass | | $7.6 \times 10^8$ |

Except where a contrary intent is expressly stated, the terms "comprises," "comprising," "containing," and "having" and the like mean "includes," "including," and the like, and are generally interpreted to be open ended transition terms. The recitation of components, structures, steps, or the like specifically listed following an open-ended transition term in no way limit such claim to the components, structures, steps, or the like specifically listed. The terms "consisting of" or "consists of" are closed transition terms.

Except where a contrary intent is expressly stated, if a method is described herein as comprising a series of steps, the order of such steps as presented herein is not necessarily the only order in which such steps may be performed, and certain of the stated steps may possibly be omitted and/or certain other steps not described herein may possibly be added to the method.

Except where a contrary intent is expressly stated, terms are used in their singular form for clarity and are intended to include their plural form.

Occurrences of the phrase "in one embodiment," or "in one aspect," herein do not necessarily all refer to the same embodiment or aspect.

The following is a list of reference numerals used throughout this specification.

US 12,691,033 B2

9

10 Straight-walled vial system
12 stopper
121 head
122 neck
123 slot
14 straight-walled vial
141 side wall
142 inner surface
143 bottom wall
144 inner volume
145 collar
146 slot
16 seal
20 cake While this invention has been described as having designs illustrated by embodiments and examples, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A straight-walled vial system (10) comprising:
a straight-walled vial (14); and
a solid lyophilized vaccine composition within the straight-walled vial (14), wherein the solid lyophilized vaccine composition comprises an antigen and a stabilizer, wherein the stabilizer comprises i SGGK3, and wherein the solid lyophilized vaccine composition is a cake (20).

2. The straight-walled vial system (10) of claim 1, wherein the straight-walled vial (14) comprises a bottom wall (143), a side wall (141) connected to and extending from the bottom wall (143), and a collar (145) extending radially outwardly from the side wall at an open end of the side wall, opposite the bottom wall.

3. The straight-walled vial system (10) of claim 1, further comprising a stopper (12) insertable through the open end.

4. The straight-walled vial system (10) of claim 3, further comprising a seal (16), wherein the seal (16) is plastic or aluminum.

5. The straight-walled vial system (10) of claim 1, wherein the antigen source is animal, human, fish, bird, microorganism, parasite, protozoal, spirochete, bacterial, viral, vector, recombinant, or combination thereof; and
the antigen is a nucleic acid, protein, peptide, or combination thereof.

6. The straight-walled vial system (10) of claim 1, wherein the antigen source is *Bordetella bronchiseptica*.

7. The straight-walled vial system (10) of claim 1, wherein the antigen source is selected from the group consisting of *Bordetella bronchiseptica* (Bb), Rabies Virus, Canine Influenza Virus (CIV), Canine Adenovirus-2 (CAV2), Canine Adenovirus-1 (CAV1), Canine Distemper Virus (CDV), Canine Parainfluenza Virus (CPiV), Canine Parvo Virus (CPV), Feline Calicivirus (FCV), Feline Herpes Virus (FHV), Feline Panleukopenia Virus (FPL), Feline leukemia Virus (FeLV), *Borrelia, Ehrlichia*, and Giardia.

8. The straight-walled vial system (10) of claim 1, wherein the composition further comprises an adjuvant, an immunoadjuvant, an immunomodulator, or a combination thereof.

9. The straight-walled vial system (10) of claim 1, wherein the stabilizer further comprises mannitol, xanthan gum, a bulking agent, or any combination thereof.

10. The straight-walled vial system (10) of claim 1, wherein the solid lyophilized vaccine composition further comprises a blending diluent comprised of MEM Powder, Sodium Bicarbonate, HEPES Acid, and purified water.

11. The straight-walled vial system (10) of claim 1, wherein the cake is configured to be removed from the straight-walled vial (14) without cracking or breaking.

12. The straight-walled vial system (10) of claim 1, wherein the straight-walled vial (14) is a glass vial.

13. The straight-walled vial system (10) of claim 1, wherein the stabilizer further comprises i) a mucoadhesive agent, ii) an agent that enhances mucosal permeability, or iii) a combination thereof.

14. A method for preparing a solid lyophilized vaccine composition, the method comprising:
combining an antigen and a stabilizer to obtain a blend, wherein the stabilizer comprises SGGK3;
filling a straight-walled vial (14) with the blend;
lyophilizing the blend in the straight-walled vial (14) to form a solid lyophilized vaccine composition; and
removing the solid lyophilized vaccine composition from the straight-walled vial (14).

15. The method of claim 14, wherein the solid lyophilized vaccine composition is for use in a human, fish, bird, cow, pig, cat, dog, horse, rabbit, or wild animal.

16. The method of claim 14, wherein the antigen is *Bordetella bronchiseptica* and the solid lyophilized vaccine composition is for use in a dog, cat, or rabbit.

17. The method of claim 14, further comprising adding mannitol to the blend of antigen and stabilizer and further comprising annealing the blend at −25° C. prior to removing the solid lyophilized vaccine composition.

18. The method of claim 14, wherein the solid lyophilized vaccine composition has a smaller diameter than the inner surface (142) of the straight-walled vial (14).

19. The method of claim 14, wherein the solid lyophilized vaccine composition is removed without cracking or breaking.

* * * * *